(12) United States Patent
Berg

(10) Patent No.: US 6,673,085 B1
(45) Date of Patent: Jan. 6, 2004

(54) ANASTOMOSIS TECHNIQUES

(75) Inventor: Todd A. Berg, Plymouth, MN (US)

(73) Assignee: St. Jude Medical ATG, Inc., Maple Grove, MN (US)

(*) Notice: Subject to any disclaimer, the term of this patent is extended or adjusted under 35 U.S.C. 154(b) by 81 days.

(21) Appl. No.: 09/860,847

(22) Filed: May 18, 2001

Related U.S. Application Data

(60) Provisional application No. 60/206,383, filed on May 23, 2000.

(51) Int. Cl.[7] ............................................. A61B 17/08
(52) U.S. Cl. ........................................ 606/153; 606/139
(58) Field of Search ........................... 606/153, 139

(56) References Cited

U.S. PATENT DOCUMENTS

| | | | |
|---|---|---|---|
| 5,976,178 A | | 11/1999 | Goldsteen et al. ............. 623/1 |
| 6,068,637 A | * | 5/2000 | Popov et al. ................ 606/159 |
| 6,120,432 A | | 9/2000 | Sullivan et al. ............... 600/36 |
| 2002/0082614 A1 | * | 6/2002 | Logan et al. ............... 606/139 |
| 2002/0091398 A1 | * | 7/2002 | Galdonik et al. ........... 606/153 |

FOREIGN PATENT DOCUMENTS

| | | | |
|---|---|---|---|
| WO | WO 98/16161 | 4/1998 | ........... A61B/17/36 |
| WO | WO 98/55027 | 12/1998 | ........... A61B/17/00 |
| WO | WO 00/27312 | 5/2000 | ............. A61F/2/06 |

\* cited by examiner

*Primary Examiner*—Kevin Shaver
*Assistant Examiner*—Candice C. Melson
(74) *Attorney, Agent, or Firm*—Fish & Neave; Robert R. Jackson; Hong S. Lin

(57) ABSTRACT

Methods for making an anastomotic connection between a first conduit and a second conduit in a patient. The first conduit and a second conduit of the patient are placed relatively adjacent to each other at the operative site to make a side-to-side anastomosis connection. A region is created where the first conduit and the second conduit contact each other. An adhesive is placed in the region between the two conduits. An aperture is then created in the region with a cutting instrument. A ring of sutures or other fasteners may be used in place of or in addition to the adhesive. An end-to-side anastomosis may be used instead of a side-to-side anastomosis.

27 Claims, 12 Drawing Sheets

ANASTOMOSIS TECHNIQUES

This application claims the benefit of U.S. Provisional application Ser. No. 60/206,383, filed May 23, 2000, which is incorporated by reference in its entirety herein.

BACKGROUND OF THE INVENTION

This invention relates to medical methods, and more particularly to methods for use in making anastomotic connections between tubular body fluid conduits in a patient.

There are many medical procedures in which it is necessary to make an anastomotic connection between two tubular body fluid conduits in a patient. An anastomotic connection (or anastomosis) is a connection which allows body fluid flow between the lumens of the two conduits that are connected, preferably without allowing body fluid to leak out of the conduits at the location of the connection. As just one example of a procedure in which an anastomosis is needed, in order to bypass an obstruction in a patient's coronary artery, a tubular graft supplied with aortic blood may be connected via an anastomosis to the coronary artery downstream from the obstruction. The anastomosis may be between the end of the graft and an aperture in the side wall of the coronary artery (a so-called end-to-side anastomosis), or the anastomosis may be between an aperture in the side wall of the graft and an aperture in the side wall of the coronary artery (a so-called side-to-side anastomosis (e.g., as in published Patent Cooperation Treaty ("PCT") patent application WO 98/16161, which is hereby incorporated by reference herein in its entirety)). The graft may be natural conduit, artificial conduit, or a combination of natural and artificial conduits. If natural conduit is used, it may be wholly or partly relocated from elsewhere in the patient (e.g., wholly relocated saphenous vein or partly relocated internal mammary artery). Alternatively, no relocation of the graft may be needed (e.g., as in above-mentioned application WO 98/16161 in which a length of vein on the heart becomes a "graft" around an obstruction in an immediately adjacent coronary artery). More than one anastomosis may be needed. For example, a second anastomosis may be needed between an upstream portion of the graft conduit and the aorta or the coronary artery upstream from the obstruction in that artery. Again, this second anastomosis may be either an end-to-side anastomosis or (as shown, for example, in above-mentioned application WO 98/16161) a side-to-side anastomosis. Alternatively, no second, upstream anastomosis may be required at all (e.g., if the graft is an only-partly-relocated internal mammary artery).

The currently most common technique for making an anastomosis is to manually suture the two tubular body fluid conduits together around an opening between them. Manual suturing is difficult and time-consuming, and the quality of the anastomosis that results is highly dependent on the skill of the person doing the suturing. In the case of coronary artery bypass procedures, one source of difficulty for suturing of an anastomosis may be motion of the heart. There is also increasing interest in procedures which are less invasive or even minimally invasive. Such procedures have potentially important advantages for patients, but they may increase the difficulty of performing manual suturing of an anastomosis by reducing or limiting access to the site within the patient at which the anastomosis must be made. Various examples of such less invasive or minimally invasive procedures are shown in above-mentioned application WO 98/16161, Goldsteen et al. U.S. Pat. No. 5,976,178, Sullivan et al. U.S. Pat. No. 6,120,432, published PCT patent application WO 98/55027, and Berg et al. U.S. patent application Ser. No. 09/187,364, filed Nov. 6, 1998, all of which are hereby incorporated by reference herein in their entireties.

In the case of making a conventional end-to-side anastomosis between a vein graft and the coronary artery, there are additional difficulties which may arise. First, the relative sizes of the coronary artery and the vein graft are different. For example, the coronary artery may typically have an inner diameter of about 1.0 to 3.0 mm, whereas a vein graft, such as the saphenous vein, may typically have an inner diameter of about 4.0 to 8.0 mm. This discrepancy between vessel diameters, i.e., a "caliber mismatch," may present a challenge to the physician to match the end of the relatively larger vein graft to an aperture in the side wall of the relatively smaller coronary artery. The resulting quality and amount of flow between the vein graft and the coronary artery, along with the provision of an effective hemodynamic seal between the two conduits, is often dependent upon the physician's skill in making a precise and effective junction between the two conduits.

Second, conventional end-to-side anastomosis typically joins the vein graft conduit to the coronary artery at an angle with respect to the lumen of the coronary artery, thus forming a junction at the wall of the coronary artery. Further away from this junction, the vein graft tends to lie against the heart structure, or substantially parallel to the lumen of the coronary artery. The transition of the vein graft from a substantially perpendicular juncture to the coronary artery to a substantially parallel position with respect to the coronary artery wall often occurs abruptly, which may result in kinking of the vein graft, with possibly reduced blood flow.

Third, joining vessels having relatively small diameters (e.g., 1–4 mm) presents the additional consideration of keeping the vessels open after the anastomosis has been made. It is therefore helpful to provide the anastomosis with an diameter equal to or larger than the diameter of the smaller vessel being joined. The larger anastomosis is performed in order to minimize the risk of closing off the flow due to the natural healing response. However, it is a challenge to provide a delivery system which is compatible with the dimensions of the anastomosis.

There are additional difficulties which may arise in an anastomosis procedure between a vein graft and a coronary artery. Initially, an artificial aperture, called an arteriotomy, is created in the side wall of the coronary artery. The coronary artery is pressurized during the creation of the aperture. During the suturing of the vein graft to the aperture, excessive bleeding may occur as a result of the pressure in the coronary artery. Thereafter, if the artery is ligated to control the excessive bleeding, the distal areas of the coronary artery vessel may become ischemic which means that vital organs may not receive adequate oxygenated blood. The excessive bleeding may also interfere with the physicians visual ability to accurately suture the vein graft to the aperture.

Another minimally invasive procedure for an anastomosis is using an end-to-side adhesive technique. With this technique, the end of the vein graft is attached to an opening on the coronary artery using adhesive. However, end-to-side adhesive anastomosis techniques have been unsuccessful for many reasons. First, precise positioning of the end of the vein graft and the aperture in the side of the coronary artery is required before and during the application of the adhesive. Due to the caliber mismatch, great skill of the physician is required in making an effective junction between the two conduits. Secondly, the overlap area between the two conduits is inadequate to provide the necessary strength for an effective attachment. Also, the excess flow of adhesive may be difficult to control. Therefore, the excess adhesive may enter into the aperture and the blood flow. Finally, the coronary artery may require ligation to control the excessive bleeding resulting in the distal areas of the coronary artery vessel becoming ischemic as described above.

In view of the foregoing, it is an object of this invention to provide methods that can be used to make anastomotic connections in lieu of manual suturing.

It is another object of the invention to provide methods that can be used to make anastomotic connections wherein the aperture in the vein graft is the same size as the aperture in the coronary artery.

It is still another object of the invention to provide methods that can be used to make anastomotic connections without the need for a high degree of manual suturing skill.

It is yet another object of the invention to provide methods for making anastomotic connections that are less adversely affected than manual suturing by adjacent or nearby body motion (e.g., motion of the patient's heart).

It is a further object of this invention to provide methods for facilitating the making of higher quality anastomotic connections more rapidly and with more consistent results than are possible with prior art methods and apparatus such as manual suturing.

It is another object of the invention to provide methods for making a high quality anastomotic connection when joining two conduits having different relative diameters.

It is yet another object of the invention to provide methods for making a high quality anastomotic connection having greater strength due to the overlap of the two conduits.

It is a further object of the invention to provide methods for making an anastomotic connection which does not require ligation.

It is another object of the invention to provide methods for making a high quality anastomosis which allows the conduits to be positioned in a substantially flat configuration with respect to one another (i.e., no angle between the vein graft and the coronary artery) and which prevents kinking of the conduits.

SUMMARY OF THE INVENTION

These and other objects of the invention are accomplished in accordance with the principles of the invention by providing methods for use in making an anastomosis connection between two tubular body fluid conduits in a patient.

An anastomosis technique is provided for facilitating cutting of an aperture in a first conduit and a second conduit of a patient. In a preferred embodiment of the subject invention, the first conduit is placed relatively adjacent to the second conduit at an operative site to make a side-to-side anastomosis connection.

A region is created where the first conduit and the second conduit are adjacent and contact each other. An adhesive is placed in a substantially two-dimensional area or region between the first conduit and the second conduit such that a substantially two-dimensional bonded area or region is created. The adhesive material is preferably highly bondable in a fluid environment.

The next step in the procedure is to create the aperture through the bonded region between the first conduit and the second conduit. The aperture is also preferably substantially two-dimensional, although smaller in area than the bonded region. A precisely controlled aperture size and geometry is needed to optimize the performance of the anastomosis. A diameter of the aperture is smaller than a diameter of the bonded region in order that after the aperture is created, the first conduit and the second conduit remain bonded and secured to each other annularly around the aperture.

A cutting instrument is provided for facilitating cutting the aperture in the bonded region of the two conduits. The cutting instrument may include a handle suitable for the physician performing the process to grip securely. The cutting instrument may also include a cutting mechanism that creates the aperture and removes the tissue in the bonded region. The cutting mechanism is inserted through an opening in a wall of the first conduit at an angle that is substantially perpendicular to a longitudinal axis of the second conduit and cuts the aperture in the bonded region. The tissue in the opening is re-attached using sutures once the cutting instrument is removed and the anastomosis procedure is completed.

The cutting mechanism may include a tissue holding structure, such as a stylet, which pierces and retains tissue, and a sharp-edged tubular structure, such as a rotatable coring tip, which cuts a plug of tissue retained by the stylet, thus providing the aperture for the anastomosis. The stylet may include a retention structure such as barbs for retaining the plug of tissue that is removed so that the tissue is prevented from entering the bloodstream.

In yet another preferred embodiment, the step of creating the aperture after the two conduits are connected may be utilized in an anastomosis procedure where conventional suturing techniques are used. The two conduits are manually sutured together in an end-to-side or side-to-side configuration. Once the two conduits are secured together, the aperture is formed using the steps discussed heretofore.

Further features of the invention, its nature and various advantages will be more apparent from the accompanying drawings and the following detailed description of the preferred embodiments.

DETAILED DESCRIPTION OF THE PREFERRED EMBODIMENTS

Although the invention has other possible uses, the invention will be fully understood from the following explanation of its uses in providing a bypass around an obstruction or occlusion in a patient's vascular system. Specifically, this invention is described with reference to anastomosis techniques performed in order to bypass from an aorta to a coronary artery.

Figure 1:
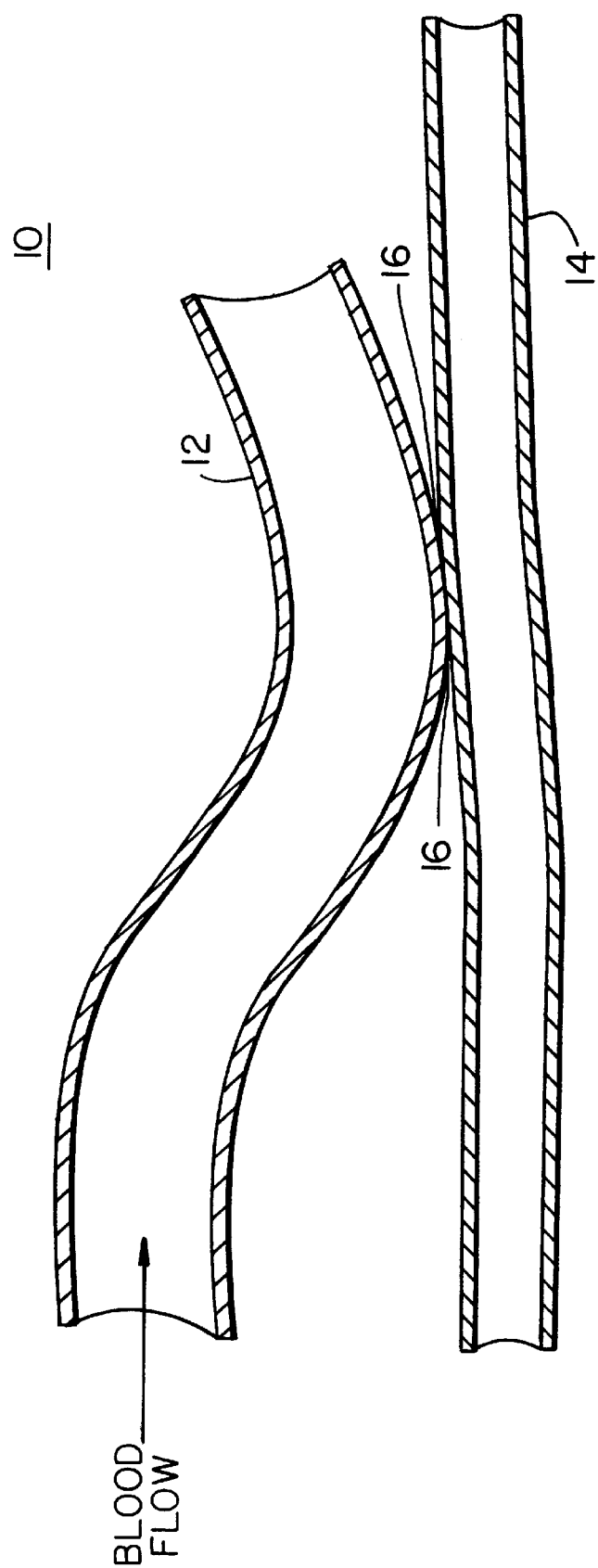
FIG. 1 is a partly sectional side view of an illustrative embodiment of an anastomosis technique in accordance with this invention.

FIG. 1 illustrates an initial step of an anastomosis procedure 10 according to the present invention. An end portion of a first conduit 12 is placed next to a second conduit 14 at an operative site to make a side-to-side anastomosis connection (See FIG. 5). The first conduit 12 is typically a graft conduit and may be a natural conduit, such as a saphenous vein graft (SVG), a partly severed internal mammery artery or similar, or an artificial conduit. The second conduit 14 is typically a patient's natural body conduit (e.g. a host artery).

The first conduit 12 is placed relatively adjacent to the second conduit 14 such that side walls of the two conduits make contact with each other. Since there is no angle between the two conduits, this arrangement allows the two conduits to be positioned in a substantially flat configuration with respect to one another which prevents kinking of the conduits. In conventional end-to-side anastomosis, kinking may occur as of result of the transition of the graft conduit from a substantially perpendicular position with the natural body conduit at the junction of the two conduits to a substantially parallel position further away from the junction. There is also no possibility of reduced blood flow as a result of kinking of the conduits.

Figure 2:
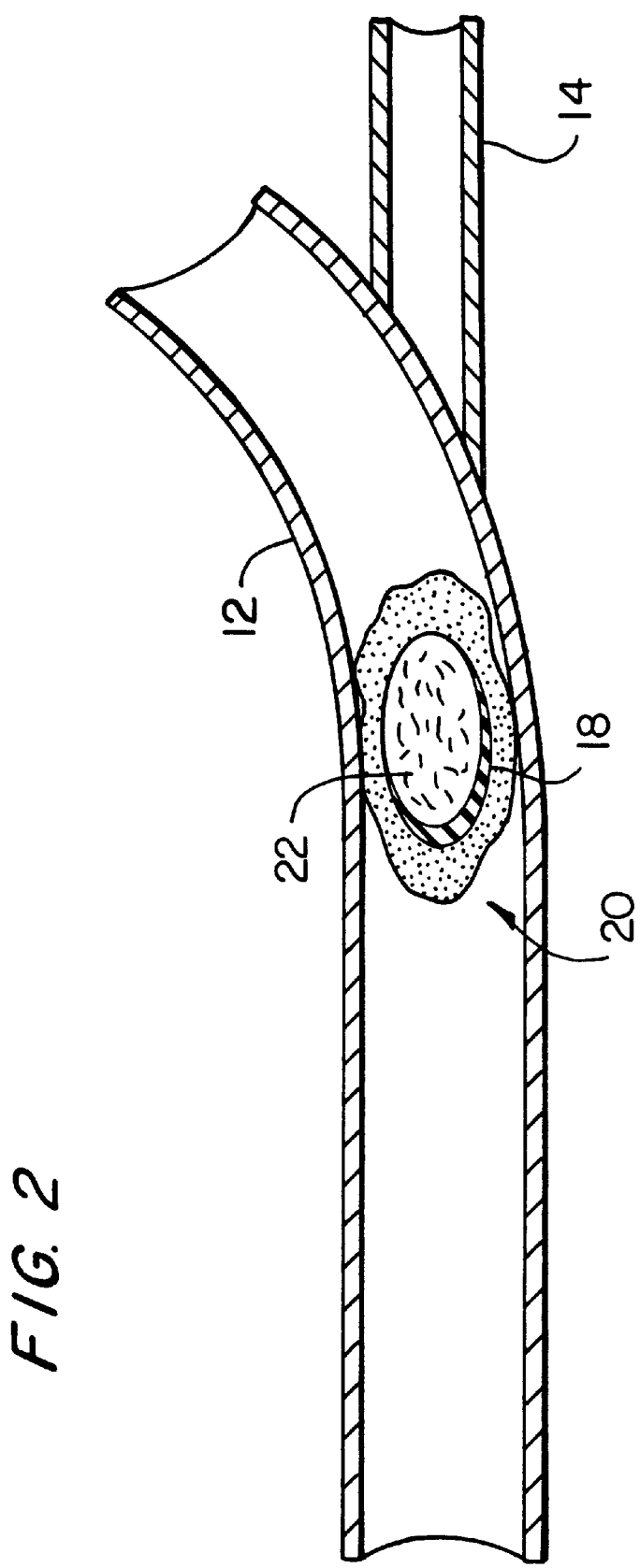
FIG. 2 is a partly sectional top view of the anastomosis technique illustrating a bonded region in accordance with this invention.

As depicted in FIGS. 1–2, a substantially two-dimensional area or region 16 is created where the first conduit 12 and the second conduit 14 are adjacent and contact each other. An adhesive material 18 (FIG. 2) is placed in the region 16 between the first conduit 12 and the second conduit 14 such that an attached and bonded region 20 which is substantially two-dimensional is created. Preferably, a side wall located near the end portion of the first conduit is attached to a side wall of the second conduit such that a side-to-side anastomosis is formed. The adhesive material 18 is preferably highly bondable in a fluid environment. A particularly preferred adhesive material is cyanoacrylate, tissue adhesive or fibrin glue, but other materials can be used instead if desired.

According to the preferred embodiment, the first conduit 12 is bonded and secured to the second conduit 14 before an aperture 22 (e.g., arteriotomy) is created in the bonded region 20. Attaching the two conduits together in conventional anastomosis procedures is the most difficult and time-consuming step. Since the two conduits in the present invention are mechanically secured together without creation of the aperture in the conduits prior to making the anastomosis connection, the procedure is performed quickly, efficiently and without bleeding due to a pressurized conduit. Also, attaching the conduits with this technique allows for a precise aperture to be formed in the two conduits, instead of the physician positioning and aligning the apertures together while suturing them together using conventional anastomosis procedures.

Figure 5:
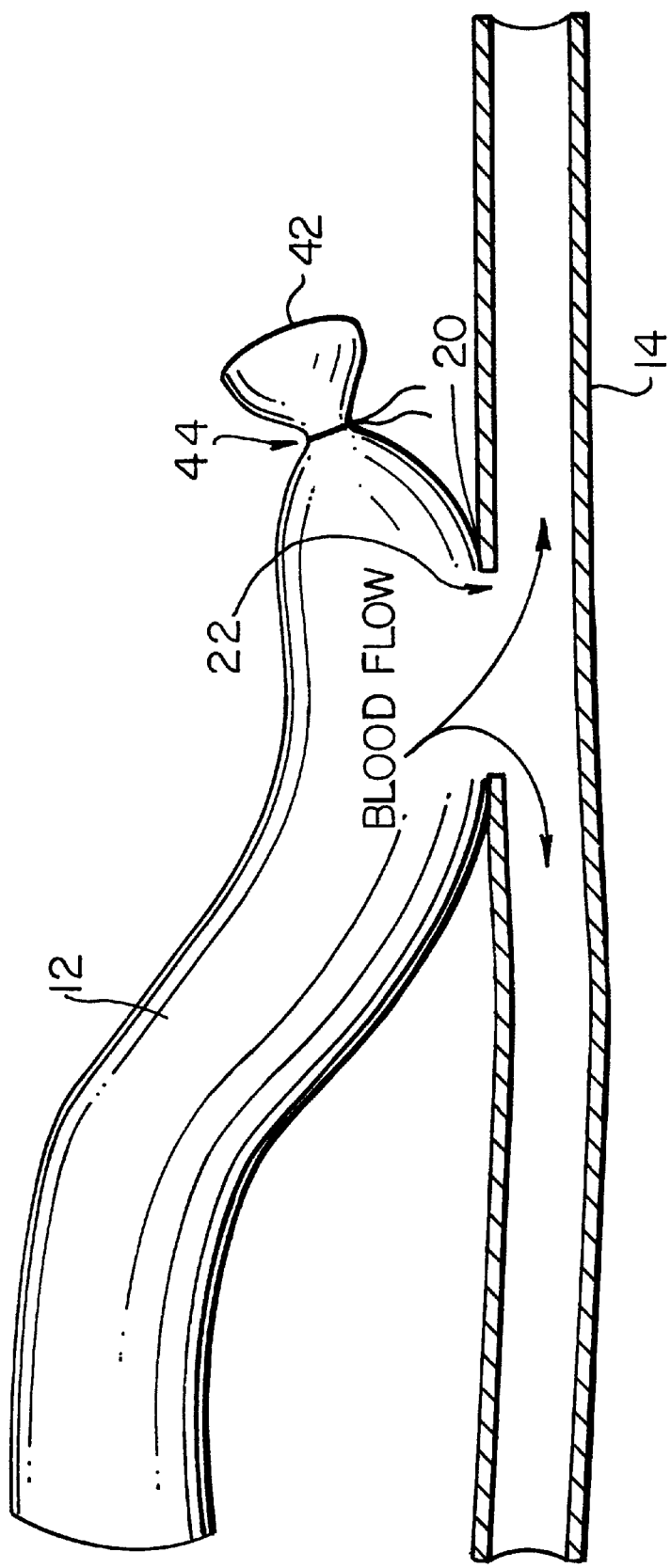
FIG. 5 is a partly sectional side view of an illustrative embodiment of a completed anastomosis technique in accordance with this invention.
Figure 6:
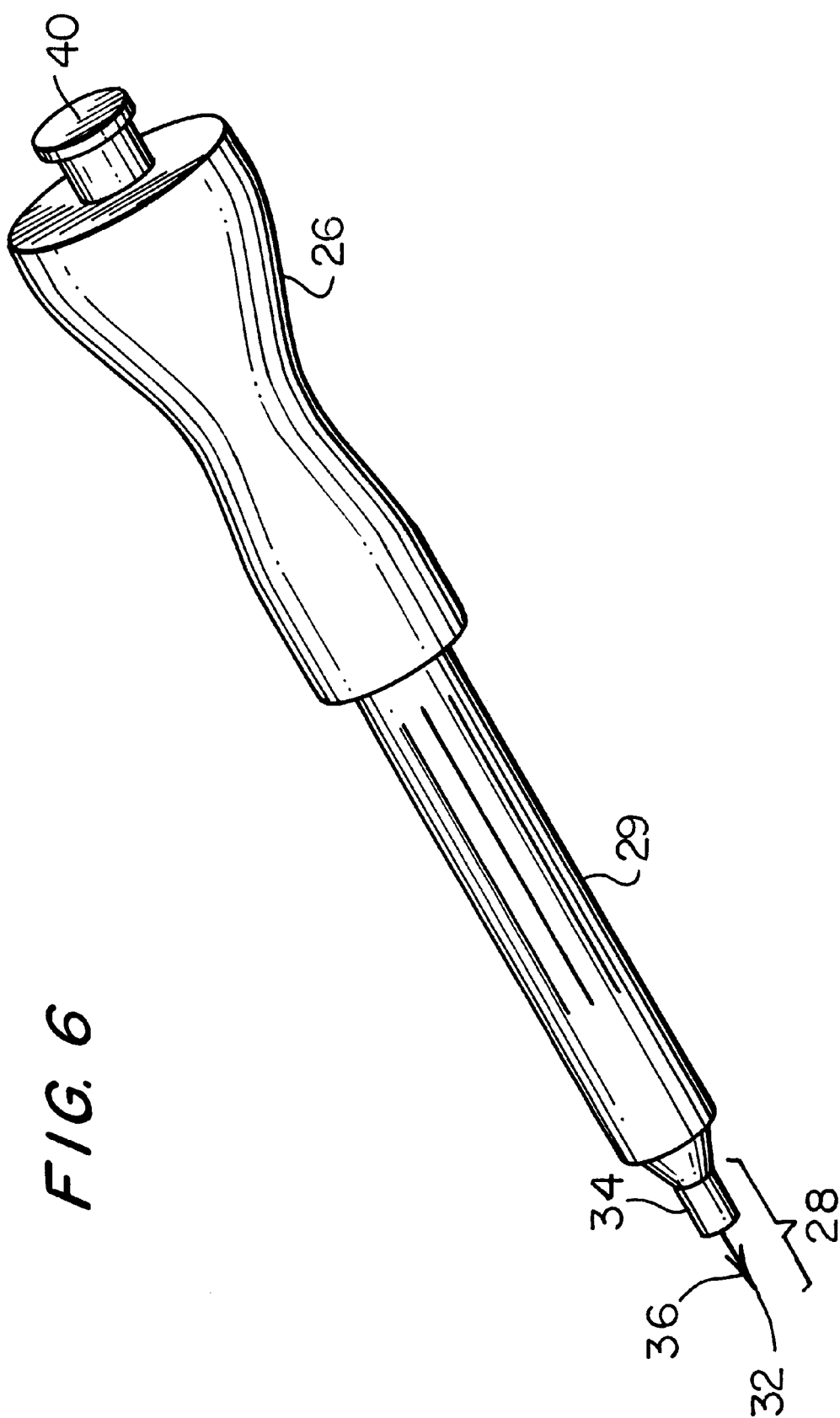
FIG. 6 is a simplified elevational view of an illustrative embodiment of a cutter instrument in accordance with the invention. Some of the components in FIG. 6 are shown enlarged relative to other components to render all components visible.

The next step in the procedure is to create the aperture 22 (as shown in FIGS. 2 and 5) through the bonded region 20 between the first conduit 12 and the second conduit 14. The aperture is also preferably substantially two-dimensional, although smaller in area than the bonded region. A precisely controlled aperture size and geometry is needed to optimize the performance of the anastomosis. A preferred anastomosis diameter is approximately the diameter of the second conduit (e.g. the host artery). The dimension may be changed depending on the size of the second conduit. A diameter of the aperture is smaller than a diameter of the bonded region in order that after the aperture is created, the first conduit and the second conduit remain bonded and secured to each other annularly around the aperture. The aperture is typically located near the end of the first conduit and downstream from an occlusion or blockage in the second conduit.

It is also to be understood that the first conduit and the second conduit may be used to make an end-to-side anastomosis, where an end portion of the first conduit is attached via adhesive to the side of the second conduit before the aperture is created in the second conduit (e.g. the patient's natural body conduit or coronary artery).

As illustrated in FIGS. 3, 4, 6–10, a cutting instrument 24 is provided for facilitating cutting the aperture 22 in the bonded region 20 of the two conduits. The cutting instrument 24 may include a handle 26 (FIG. 6) suitable for a physician performing the process to grip securely. The cutting instrument 24 also includes a cutting mechanism 28 that creates the aperture and removes the tissue in the bonded region and a rotating handle 29, described hereinafter.

Figure 3:
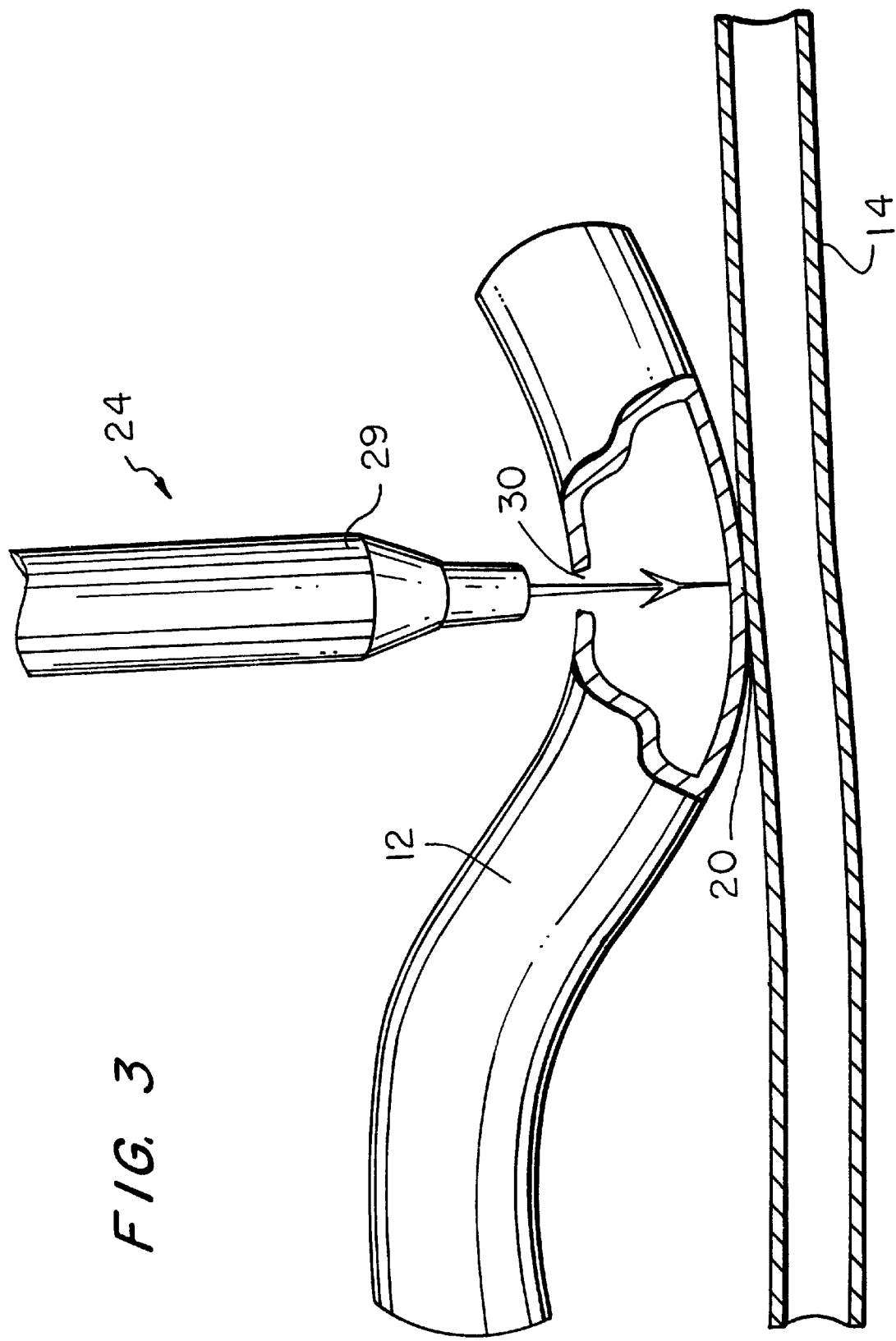
FIG. 3 is a partly sectional side view of the anastomosis technique illustrating a cutter instrument removing tissue in accordance with the invention.
Figure 4:
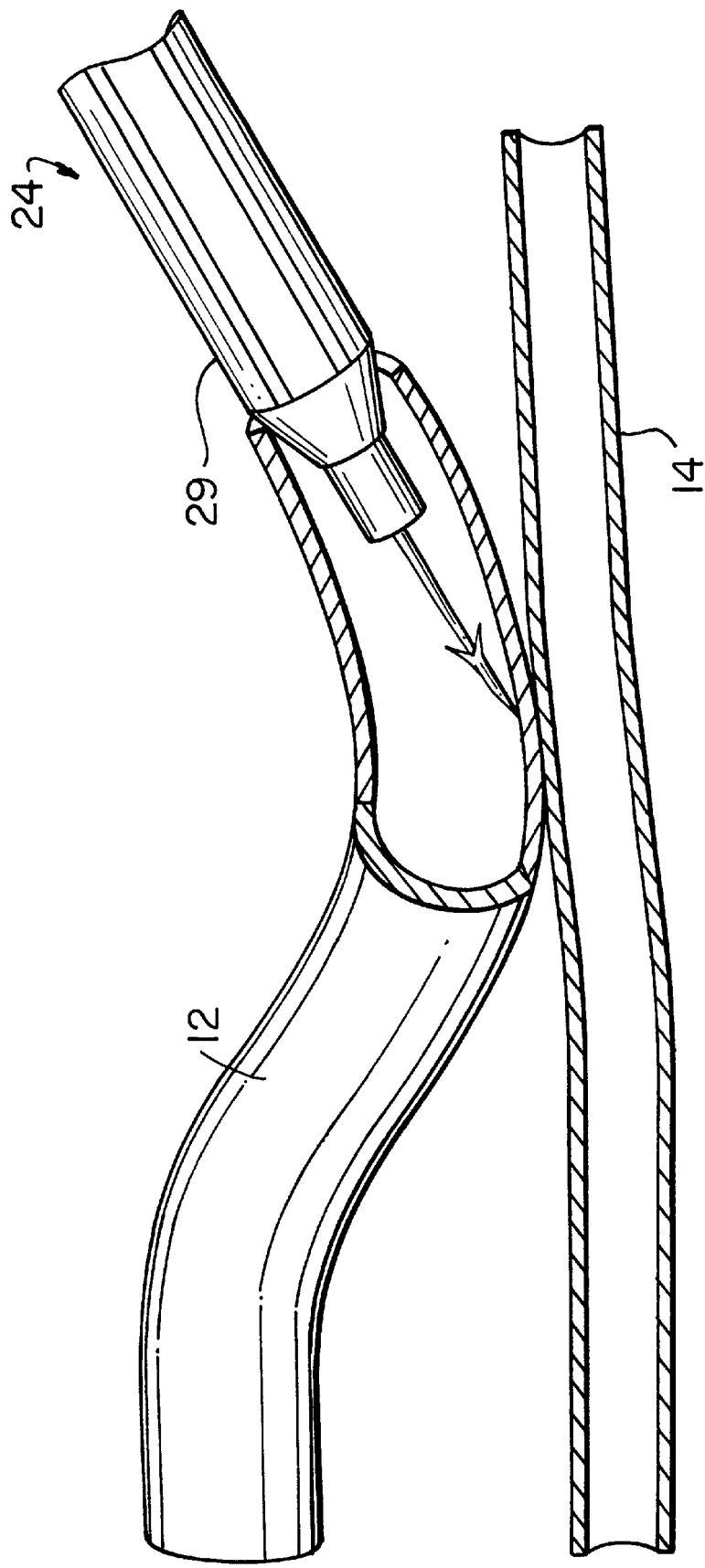
FIG. 4 is a partly sectional side view of the anastomosis technique illustrating a cutter instrument removing tissue via an end of a conduit in accordance with the invention.

As shown in FIG. 3, the cutting instrument 24 is inserted through an opening 30 in a first side wall of the first conduit 12 adjacent to the bonded region 20. The opening 30 may be created with another cutting instrument such as a scalpel. After the aperture 22 is formed in the bonded region and the anastomosis is complete, the tissue in the opening 30 is sutured closed. The cutting instrument 24 is inserted at an angle that is substantially perpendicular to a longitudinal axis of the second conduit 14. Alternatively, the cutting instrument 24 can be inserted at the end of the first conduit such that it cuts the bonded region at an angle that is acute to the longitudinal axis of the second conduit 14, as shown in FIG. 4.

With reference to FIGS. 6–10, the cutting mechanism 28 may include a tissue holding structure 32, such as a stylet, which pierces and retains tissue, and a sharp-edged tubular structure, such as a rotatable coring tip 34, which cuts the tissue retained by the stylet, thus providing the aperture for the anastomosis.

The stylet 32 may include a retention structure 36 such as barbs for retaining a plug of tissue 38 (FIGS. 9–10) that is removed so that the tissue is prevented from entering the bloodstream. Retention structure 36 may be a basically conical structure or array of members having its smaller portion pointing in the direction of the stylet 32. To facilitate passage of the retention structure 36 through the tissue at the bonded region area, the structure may include resilient members (e.g. barbs) that are attached to the remainder of the retention structure adjacent the distal end and have proximal end portions that are free and resiliently biased to spring radially out from the retention structure to which the distal portions are attached. As the stylet 32 and the retention structure 36 initially pierce and pass through the tissue, the resilient members deflect radially inwardly to reduce an effective diameter of the retention structure 36. Once through the tissue, the resilient members spring radially out and prevent tissue proximal of them from coming off the distal end of the instrument.

Figure 7:
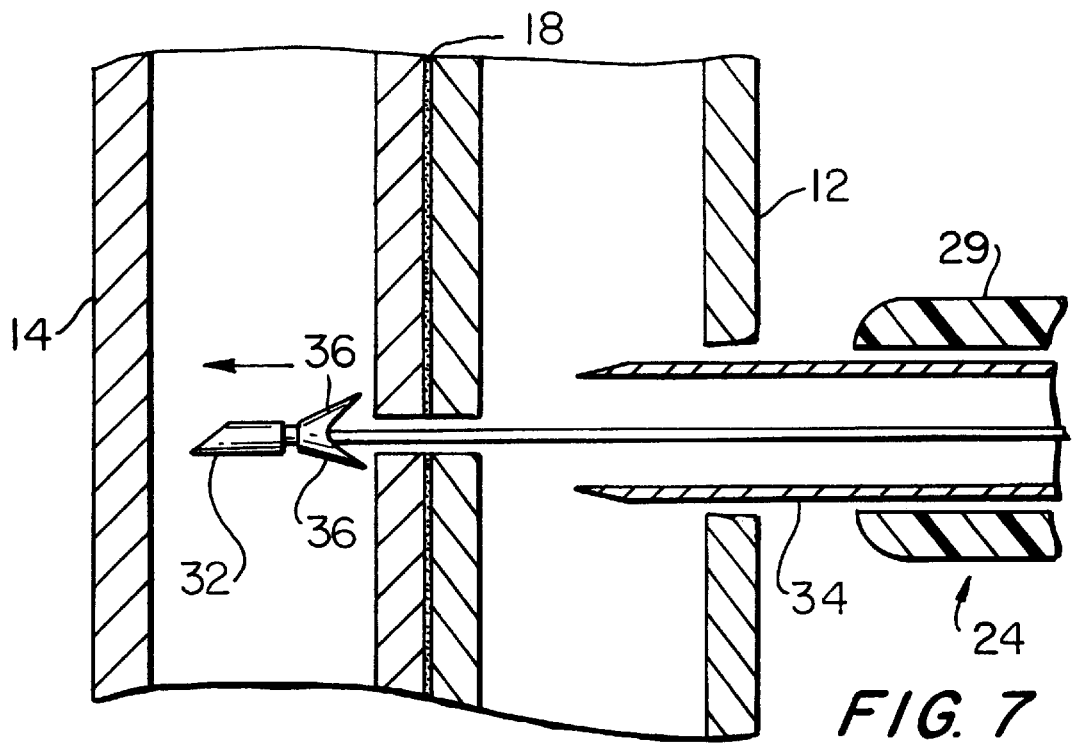
FIG. 7 is an enlarged, partly sectional view of a portion of the illustrative cutter instrument in accordance with the invention.
Figure 8:
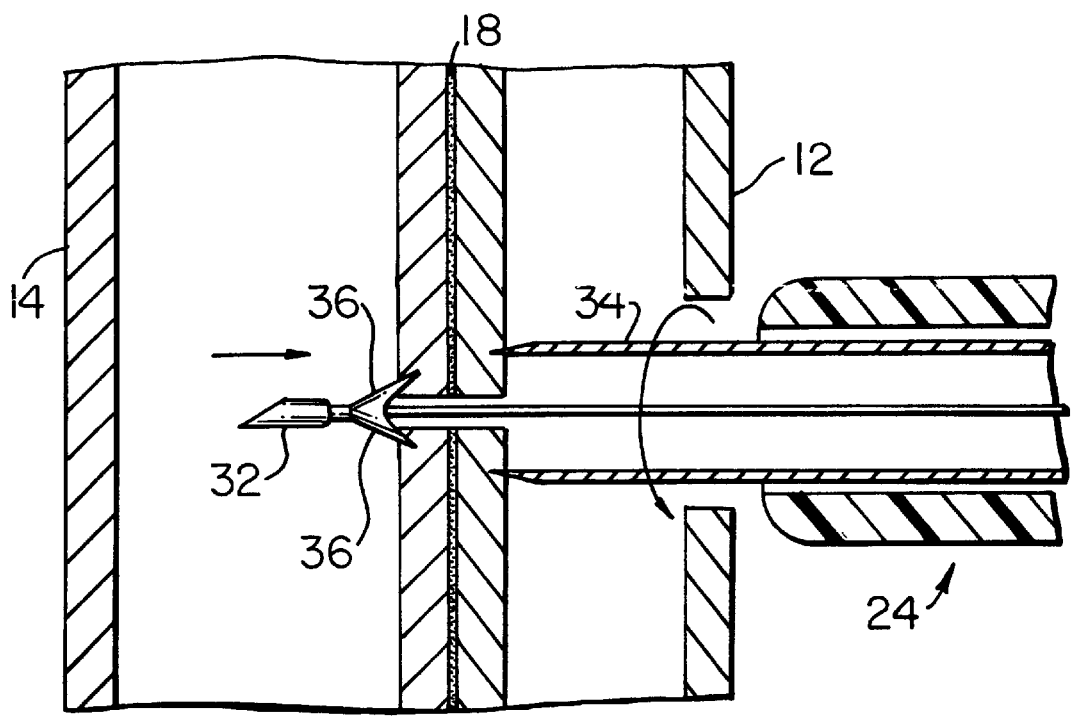
FIG. 8 is an enlarged, partly sectional view, similar to FIG. 7, in a later stage of use in accordance with the invention.
Figure 9:
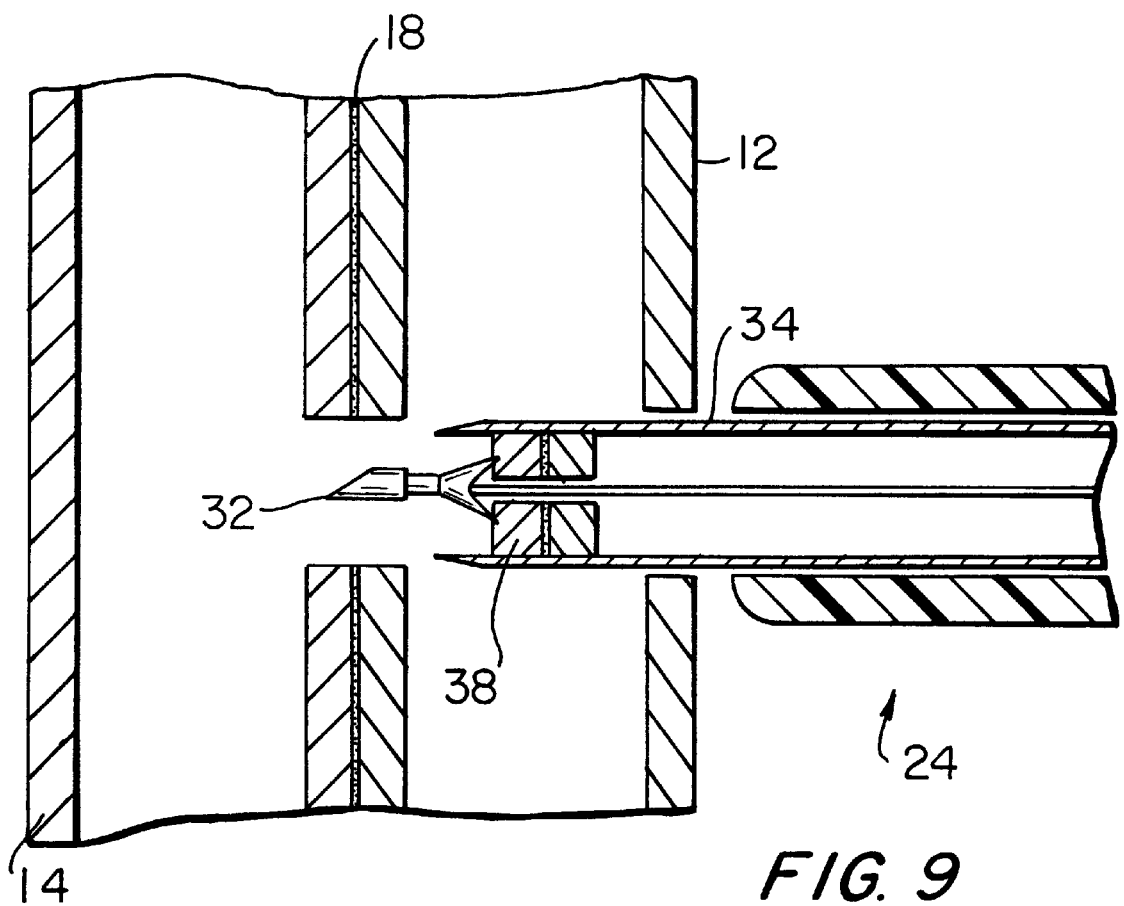
FIG. 9 is an enlarged, partly sectional view, similar to FIG. 8, in a subsequent stage of use in accordance with the invention.

The physician may depress the cutting stylet 32 via a stylet advancer 40 (FIG. 6) in order to extend the stylet 32 into the bonded region 20 of the two conduits. As illustrated in FIGS. 3–4, a tip of the stylet 32 pierces the tissue at a location in the direction indicated by the arrow. The retention structure 36 may temporarily collapse and pass through the tissue (FIGS. 7–8). Once the stylet 32 and retention structure has passed into the tissue of the bonded region 20, the physician may retract the stylet by the stylet advancer 40. Consequently, the tissue in the area of the bonded region 20 to be removed is trapped between the retention structure 36 of the stylet and a leading edge of the coring tip 34. The sharp-edged coring tip 34 is rotated manually by a rotating handle 29 in order to cut through the tissue as shown in FIG. 9.

Figure 10:
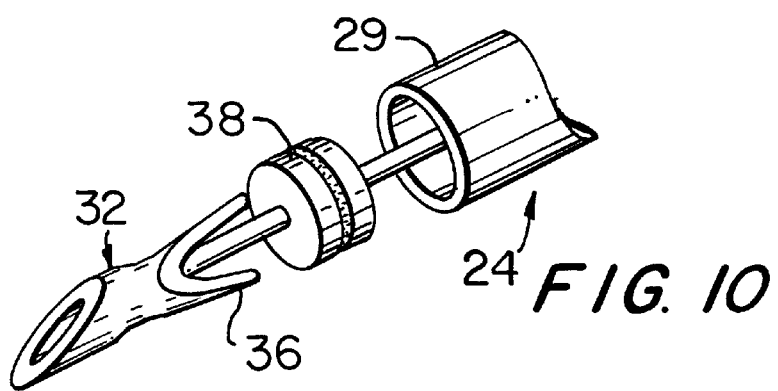
FIG. 10 is a perspective view of a portion of the illustrative cutter instrument in still a later stage of use in accordance with the invention.
Figure 11:
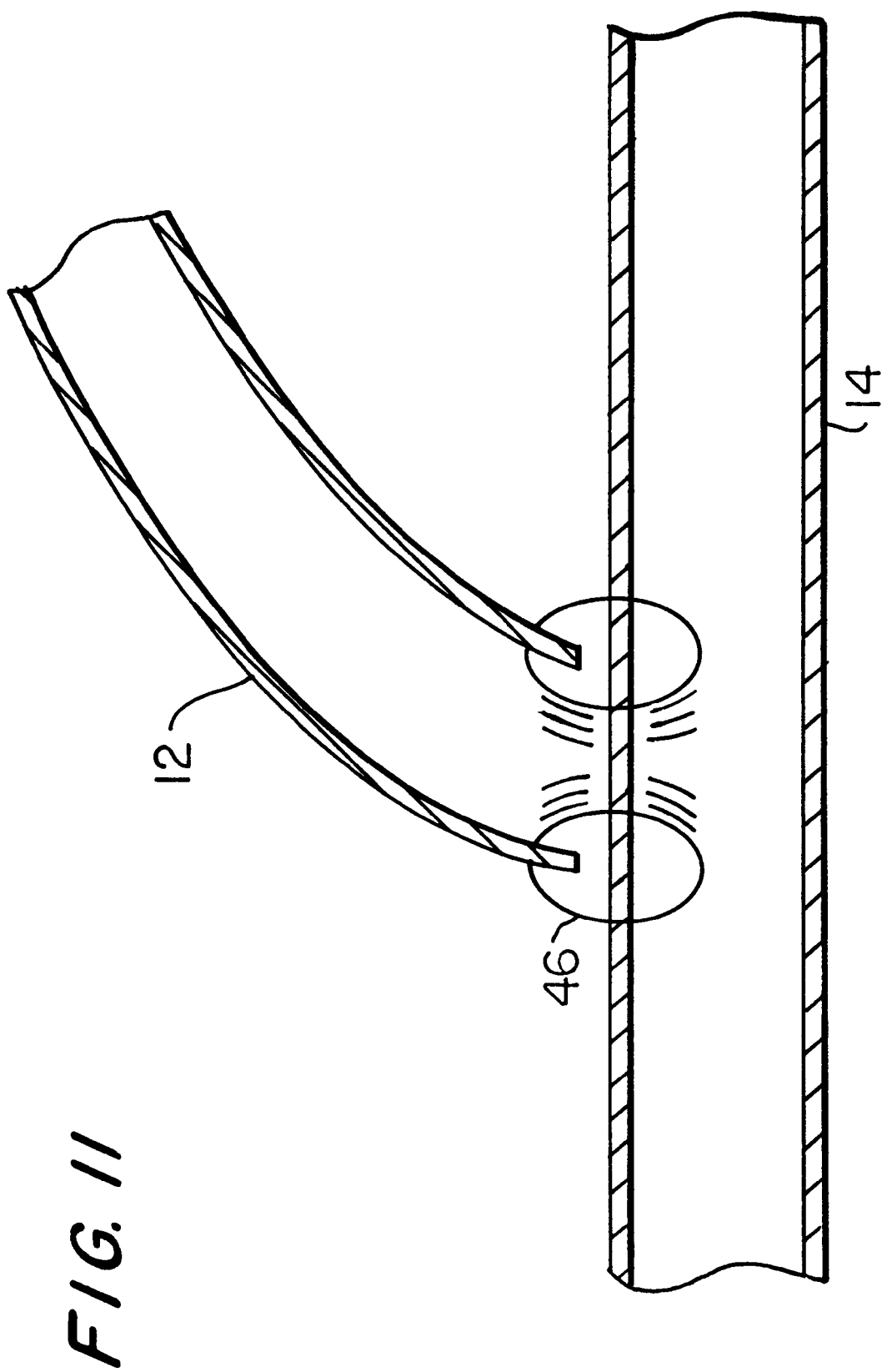
FIG. 11 is a partly sectional side view of an illustrative embodiment of a side-to-end anastomosis utilizing suturing techniques in accordance with the invention.
Figure 12:
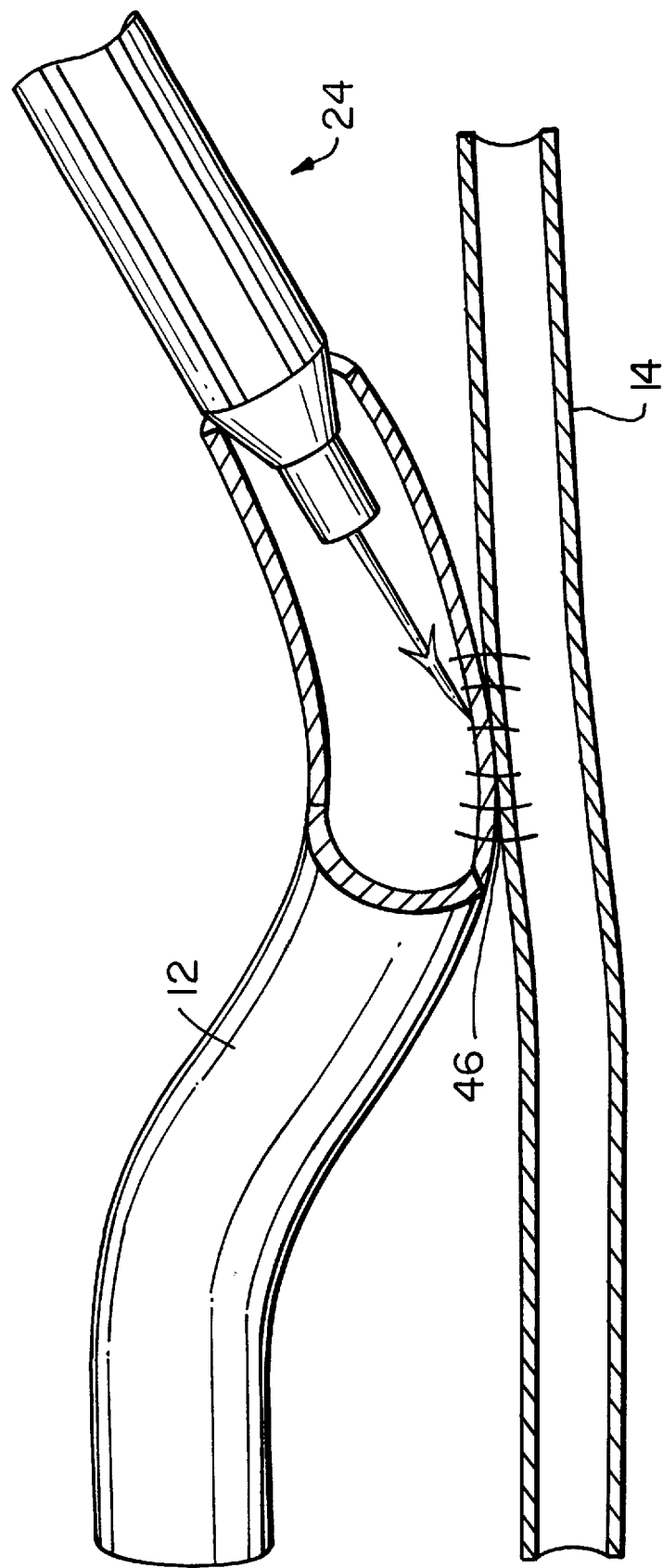
FIG. 12 is a partly sectional side view of an illustrative embodiment of a side-to-side anastomosis utilizing suturing techniques and an illustrative cutter instrument in accordance with the invention.
Figure 13:
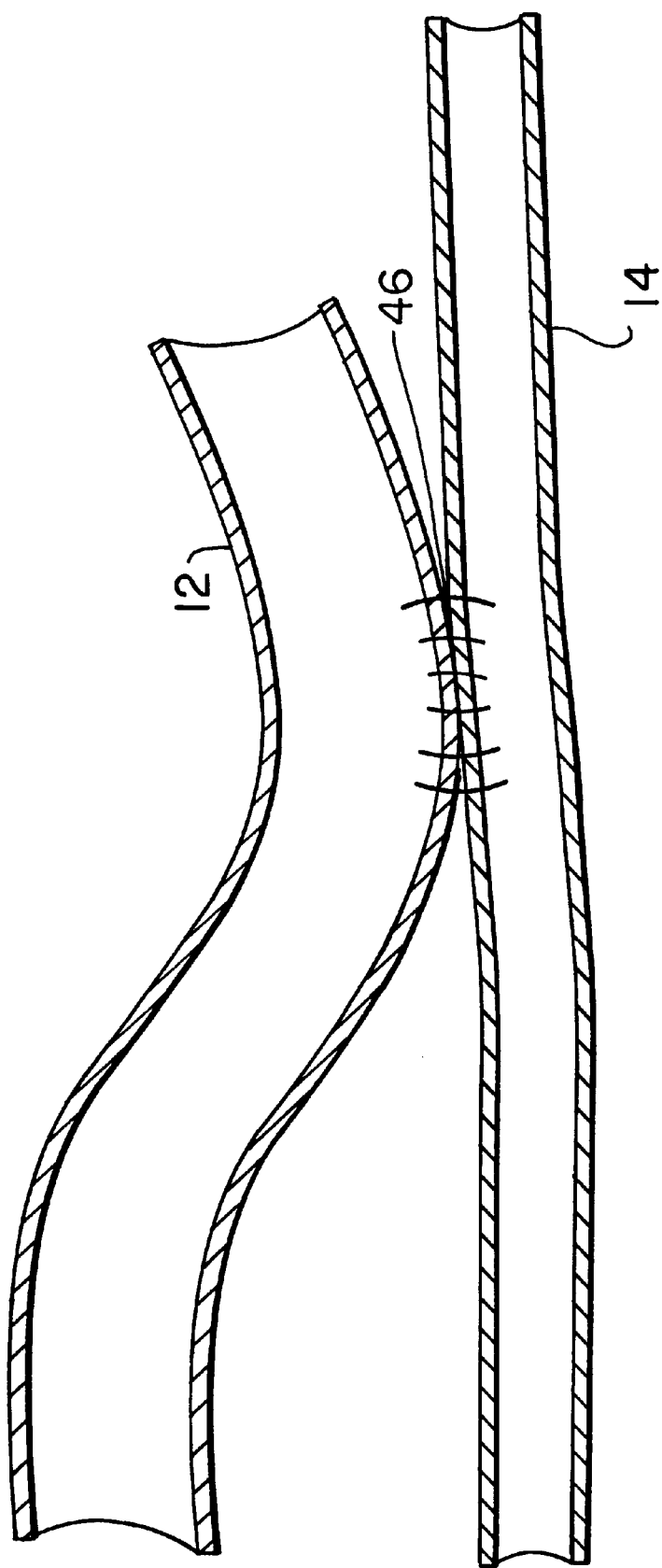
FIG. 13 is a partly sectional side view of an illustrative embodiment of a side-to-side anastomosis utilizing suturing techniques in accordance with the invention.
Figure 14:
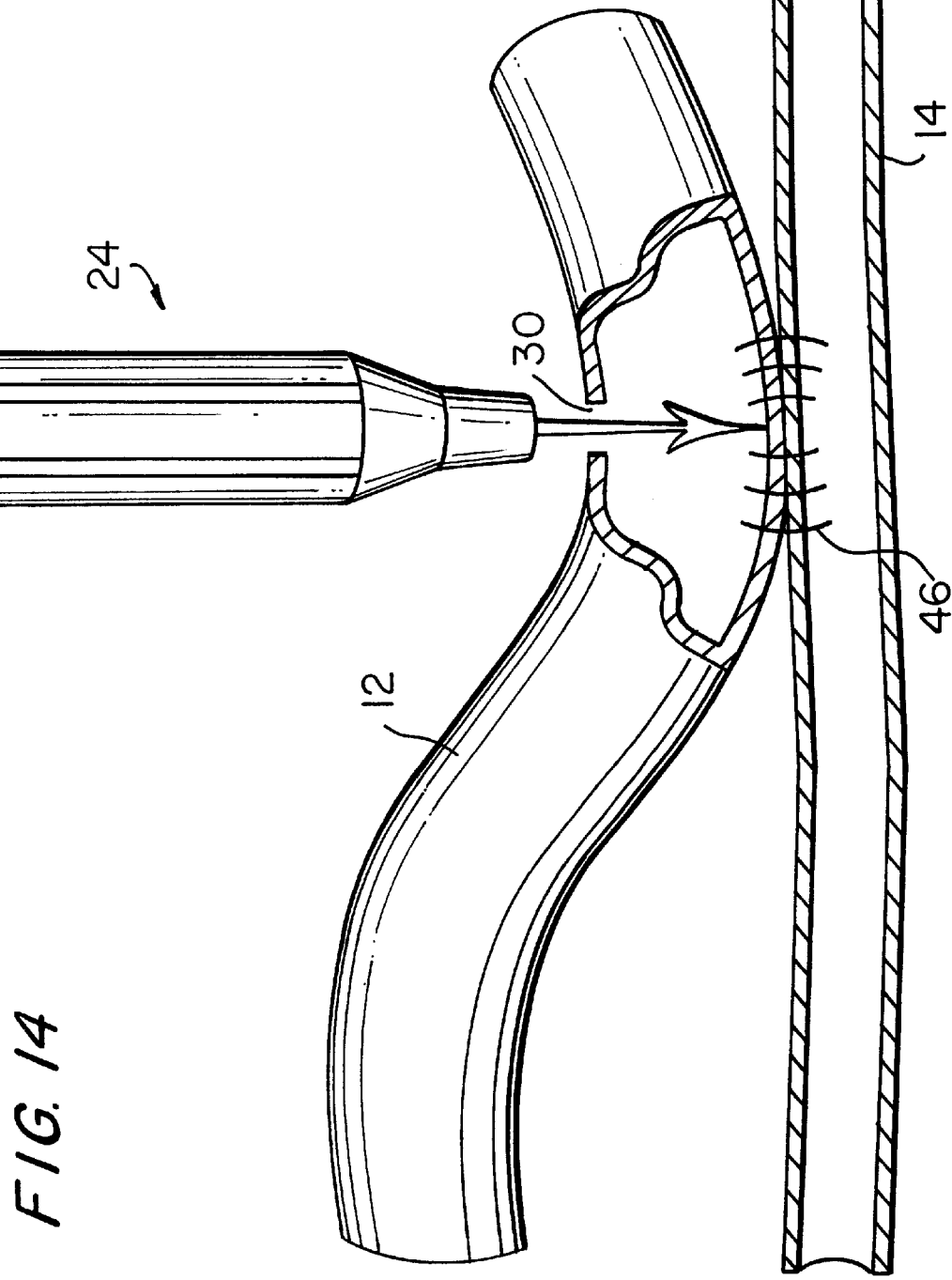
FIG. 14 is a partly sectional side view of an illustrative embodiment of a side-to-side anastomosis utilizing suturing techniques and the cutter instrument in accordance with the invention.

Once the coring tip 34 has cut through the area of the bonded region, the plug 38 of material results from the cutting. The retention structure 36 retains the plug as shown in FIG. 10. It is contemplated that other cutting devices and methods may be used to remove the tissue from the area where the aperture is created. For example, a tissue punch having retaining structures on both sides of the bonded region may be used. Once the tissue punch is inserted, a sharp-edged punch is activated severing the tissue and creating the aperture.

Once the tissue plug 38 has been severed, the anastomosis 10 is complete, and the cutting instrument (with tissue plug 38 still secured by the instrument) is removed from the operative site. The tissue in the opening 30 on the first wall of the first conduit 12 is thereafter sewn closed with sutures. As depicted in FIG. 5, an open end 42 of the first conduit 12 is subsequently tied off by a surgical string or suture 44 (e.g. a ligature) allowing for smooth and direct blood flow from the first conduit to the second conduit. A fluid-tight anastomotic connection between the conduits is thereby formed. It is understood that other methods for securing the end of the conduit may be used as long as fluid is prevented from flowing through the end.

Using the present invention, the physician creates a substantially circular aperture, which promotes smooth blood flow and rapid healing. Since the aperture is created after the conduits are secured to each other, the risk of adhesive obstructing flow in the conduits is eliminated. Also, no foreign materials, such as sutures or connectors, are present in the fluid pathway. By providing a procedure for side-to-side anastomosis, significant overlap of the two conduits is provided, producing significant contact area and thereby strengthening the anastomosis.

It is also to be understood that the step of creating the aperture after the two conduits are connected may be utilized in an anastomosis procedure where conventional suturing or other similar techniques are used, as shown in FIGS. 11–14. In this embodiment, the two conduits are manually sutured together in an end-to-side (FIG. 11) or side-to-side configuration (FIGS. 12–14) using sutures 46. The sutures collectively form a hollow annular ring surrounding the tissue that will later be cut away and removed to form an aperture that provides fluid communication between the lumens of the two conduits. Once the two conduits are secured together, the aperture is formed using the cutting instrument 24 with the steps discussed with reference to FIGS. 7 to 10. This prevents excessive bleeding because a fluid-tight connection surrounding the eventual cut-through aperture is made before the aperture is formed between the two conduits. Also, an adhesive is not utilized for connecting the two conduits. Therefore, foreign materials are prevented from entering the blood pathway. It will be understood, however, that an adhesive can be used in addition to suturing, if desired.

It will be understood that the foregoing is only illustrative of the principles of the invention and that various modifications can be made by those skilled in the art without departing from the scope and spirit of the invention. For example, the invention can be used to add a graft to the patient's circulatory system elsewhere than between the aorta and a coronary artery as has been specifically described and shown heretofore.

What is claimed is:

1. A method for making an anastomotic connection between a side wall of a first conduit and a side wall of a second conduit, comprising:
    attaching the first conduit to the second conduit, wherein an attached region is created; and
    making an aperture in the attached region after the creation of the attached region;
    the first conduit and the second conduit forming a fluid-tight anastomotic connection therebetween.

2. The method as defined in claim 1, wherein the first conduit and the second conduit are relatively adjacent to each other.

3. The method as defined in claim 1, wherein attaching the first conduit to the second conduit comprises placing an adhesive between the first conduit and the second conduit.

4. The method as defined in claim 1, wherein attaching the first conduit to the second conduit comprises suturing the first conduit to the second conduit.

5. The method as defined in claim 1, further comprising:
    after attaching the first and second conduits, closing an end portion of the first conduit.

6. The method as defined in claim 1, wherein creating the aperture in the attached region comprises severing tissue using a cutting instrument.

7. The method as defined in claim 6, wherein the cutting instrument further comprises cutting the tissue with a rotatable coring tip.

8. The method as defined in claim 6, further comprising inserting the cutting instrument through an end of the first conduit.

9. The method as defined in claim 6, wherein the cutting instrument further comprises retaining the severed tissue in the attached region using a tissue holding structure.

10. The method as defined in claim 9, wherein the tissue holding structure further comprises preventing the severed tissue from entering a patient's bloodstream using a retention structure.

11. The method as defined in claim 6, further comprising inserting the cutting instrument through an opening in a wall of the first conduit.

12. The method as defined in claim 11, further comprising:
    after attaching the first and second conduits, closing the opening in the wall of the first conduit.

13. A method for creating an anastomotic connection between tubular conduits in a patient, comprising:
    attaching a side wall of a first conduit to a side wall of a second conduit;
    creating an attached region using an adhesive; and
    making an aperture in the attached region using a cutting instrument after the creation of the attached region;
    the first conduit and the second conduit forming a fluid-tight anastomotic connection therebetween.

14. The method as defined in claim 13, wherein the cutting instrument further comprises cutting the tissue with a rotatable coring tip.

15. The method as defined in claim 13, further comprising inserting the cutting instrument through an end of the first conduit.

16. The method as defined in claim 13, further comprising:
    after attaching the first and second conduits closing an end portion of the first conduit.

17. The method as defined in claim 13, wherein the cutting instrument further comprises retaining the severed tissue in the attached region using a tissue holding structure.

18. The method as defined in claim 17, wherein the tissue holding structure further comprises preventing the severed tissue from entering a patient's bloodstream using a retention structure.

19. The method as defined in claim 13, further comprising inserting the cutting instrument through an opening in a wall of the first conduit.

20. The method as defined in claim 19, further comprising:
    after attaching the first and second conduits, closing the opening in the wall of the first conduit.

21. A method for creating an anastomotic connection between tubular conduits in a patient, comprising:
    attaching a sidewall of a first conduit to a sidewall of a second conduit;
    creating an attached area using a suturing technique; and
    making an aperture between the first conduit and the second conduit within the attached area using a cutting instrument after the creation of the attached region;
    the first conduit and the second conduit forming a fluid-tight anastomotic connection therebetween.

22. The method as defined in claim 21, wherein the cutting instrument further comprises cutting the tissue with a rotatable coring tip.

23. The method as defined in claim 21, further comprising:
    after attaching the first and second conduits, closing an end portion of the first conduit.

24. The method as defined in claim 21, wherein the cutting instrument further comprises retaining the severed tissue using a tissue holding structure.

25. The method as defined in claim 24, wherein the tissue holding structure further comprises preventing the severed tissue from entering a patient's bloodstream using a retention structure.

26. The method as defined in claim 21, further comprising inserting the cutting instrument through an opening in a wall of the first conduit.

27. The method as defined in claim 26, further comprising:
    after attaching the first and second conduits, closing the opening in the wall of the first conduit.

* * * * *